United States Patent
Osborn, III et al.

(10) Patent No.: US 6,254,584 B1
(45) Date of Patent: *Jul. 3, 2001

(54) THIN COMFORTABLE INTERLABIAL ABSORBENT STRUCTURE

(75) Inventors: Thomas Ward Osborn, III, Cincinnati, OH (US); Katherine Louise Mayer, Newport, KY (US); Letha Margory Hines, Cincinnati; Edward J. Milbrada, West Chester, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/778,521

(22) Filed: Jan. 3, 1997

(51) Int. Cl.[7] ...................................... A61F 13/15
(52) U.S. Cl. .................. 604/385.17; 604/358; 604/364; 604/378; 604/379; 604/387; 604/904; 604/385.18
(58) Field of Search ..................... 604/358, 364, 604/378, 379, 385.1, 387, 385.17

(56) References Cited

U.S. PATENT DOCUMENTS

| | | |
|---|---|---|
| 2,917,049 | 12/1959 | Delaney . |
| 3,667,466 | 6/1972 | Ralph . |
| 3,726,277 | 4/1973 | Hirschman . |
| 3,857,394 * | 12/1974 | Alemary ...................... 604/385.1 X |
| 4,046,147 * | 9/1977 | Berg ................... 604/385.1 |
| 4,595,392 | 6/1986 | Johnson et al. ................ 604/385.1 |
| 4,631,062 | 12/1986 | Lassen et al. .................... 604/385 R |
| 4,673,403 * | 6/1987 | Lassen et al. .................... 604/385.1 |
| 4,737,582 * | 4/1988 | Goldman et al. ................ 604/364 X |
| 4,950,264 | 8/1990 | Osborn, III ....................... 604/385.1 |
| 5,074,855 * | 12/1991 | Rosenbluth et al. ............. 604/385.1 |
| 5,171,302 * | 12/1992 | Buell ................................ 604/385.1 |
| 5,230,119 * | 7/1993 | Woods et al. ..................... 604/385.1 |
| 5,484,429 | 1/1996 | Vukos et al. ...................... 604/385.1 |
| 5,558,656 | 9/1996 | Bergman .......................... 604/385.1 |
| 5,827,258 * | 10/1998 | McFall et al. .................... 604/385.1 |
| 5,885,265 * | 3/1999 | Osborn et al. .................... 604/385.1 |
| 5,891,126 * | 4/1999 | Osborn et al. .................... 604/385.1 |
| 5,895,381 * | 4/1999 | Osborn ............................. 604/385.1 |
| 5,916,205 * | 6/1999 | Olson et al. ...................... 604/385.1 |
| 5,968,026 * | 10/1999 | Osborn et al. . |

FOREIGN PATENT DOCUMENTS

| | | | |
|---|---|---|---|
| 2059096 * | 7/1993 | (CA) | ............................... 604/385.1 |
| 4032119 | 4/1992 | (DE) . | |
| 0 711 870 A1 | 5/1996 | (EP) . | |
| WO 93/15700 | 8/1993 | (WO) . | |
| WO 95/17148 | 6/1995 | (WO) . | |
| WO 96/07379 | 3/1996 | (WO) . | |

* cited by examiner

Primary Examiner—John G. Weiss
Assistant Examiner—Paul Shanoski
(74) Attorney, Agent, or Firm—Edward Milbrada; Matthew P. Fitzpatrick; Jeffrey V. Bamber

(57) ABSTRACT

An interlabial absorbent structure is disclosed. The interlabial absorbent structure comprises a pair of absorbent panels that are sufficiently flexible such that the panels can, at least partially, conform to the walls of a wearer's interlabial space. The panels are joined by an isthmus which is positioned farthest into a wearer's interlabial space when the interlabial absorbent product is worn. Alternative embodiments of the isthmus are also described which direct bodily fluids that are deposited thereon along the longitudinal length of the interlabial absorbent structure.

3 Claims, 2 Drawing Sheets

THIN COMFORTABLE INTERLABIAL ABSORBENT STRUCTURE

FIELD OF THE INVENTION

The present invention is directed to an absorbent articles such as catamenial devices, incontinence pads, or the like. More particularly, the present invention is directed to interlabial absorbent structures that are thin and flexible such that they conform to and remain in contact with the walls of a wearer's interlabial space.

BACKGROUND OF THE INVENTION

Disposable absorbent articles have been commercially available for many years and have met with great success world wide. For example, continuing improvements to catamenial devices have freed women from much of the inconvenience of their monthly menstrual period. However, further improvements are still needed.

One class of catamenial device, interlabial pads, has the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is the Fresh 'n Fit® Padette which is marketed by ATHENA Medical Corp. of Portland, Oreg. and described in U.S. Pat. Nos. 3,983,873 and 4,175,561 issued to Hirschman on Oct. 5, 1976 and Nov. 27, 1979 respectively.

However, many of these devices have not met with great commercial success. There are drawbacks associated with all of the devices listed above. For example, the device described in the Delaney patent does not appear to be capable of easy insertion, due to the possibility of the layers of absorbent material opening up during insertion. The commercially available Padette product may cause wearer discomfort even if properly inserted. Also, the Padette product may not completely cover the urethra or the vaginal introitus and may not provide protection when a wearer squats. Thus, there is opportunity to provide an improved interlabial pad.

The walls of the interlabial space are quite convoluted with many folds and wrinkles. Thus, it is desirable to provide interlabial absorbent structures having flexibility such that the absorbent structure can conform, at least partially, to the walls of a wearer's interlabial space. Such conformity, particularly throughout a wide range of wearer motions, can result in improved retention of bodily fluids in the absorbent structure and less risk of leakage and staining of undergarments, clothing, or bedding.

Also, because the volume of the interlabial space is small, an interlabial device should be sized so as not to exert undue pressure on the walls thereof Otherwise, a wearer may experience discomfort due to improper sizing. Such sizing should also take into account the possibility that, when a fresh interlabial device is inserted, it may not be inserted in an optimal position for comfort.

Thus, it is an object of the present invention to provide an interlabial absorbent structure with performance properties (such as wearer comfort, leakage resistance, and the like) equaling or exceeding those of contemporary interlabial devices. It is a further object of this invention to provide an interlabial absorbent structure that has sufficient flexibility to conform to the convoluted surface of a female wearer's interlabial space and remain in contact therewith throughout a wide range of wearer movements. It is still a further object of the present invention to provide an interlabial absorbent structure having a volume and mechanical properties such that the device exerts minimal pressure on the walls of a wearer's interlabial space (i.e. the inner surfaces of the labia minora and maxima).

SUMMARY OF THE INVENTION

This invention relates to absorbent structures. More particularly, the invention relates to an absorbent structure that is worn interlabially by female wearers for catamenial purposes, incontinence protection, or for other non menstrual vaginal discharges.

In a preferred embodiment of the present invention, the interlabial absorbent structure comprises a pair of absorbent panels that are joined by a longitudinally extending isthmus. In use the isthmus is inserted into a wearer's interlabial space such that it is in proximity to her vestibule floor. The panels extend laterally outward from the isthmus and contact the walls of the wearer's vaginal vestibule providing resistance to leakage around the interlabial absorbent structure.

The absorbent panels are sufficiently flexible such that they at least partially conform to the convoluted surface of the walls of the interlabial space. This flexibility also allows the interlabial absorbent structure to respond to a wide range of wearer movement without becoming a source of discomfort to the wearer. The panels also have sufficient absorbent capacity provided with sufficient absorbency to absorb and retain exudates discharged from a wearer's body. Preferably, each panel comprises a fibrous web. More preferably, each panel comprises a tissue web.

The isthmus joins the proximal edges of the panels to form the interlabial absorbent structure. The isthmus can comprise an extension of the panels or a separate element to which the panels are joined. Preferably, the isthmus comprises an extension of the panels. In a preferred embodiment, the isthmus also directs any fluids that may be deposited thereon to flow in the longitudinal direction making fuller use of the absorbent capacity of the panels. In various embodiments this flow directing property can be provided by a densified portion of the fibrous structure, a "V" shaped channel, or an extension of the plurality of plies of tissue that comprise the preferred embodiment of each panel.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
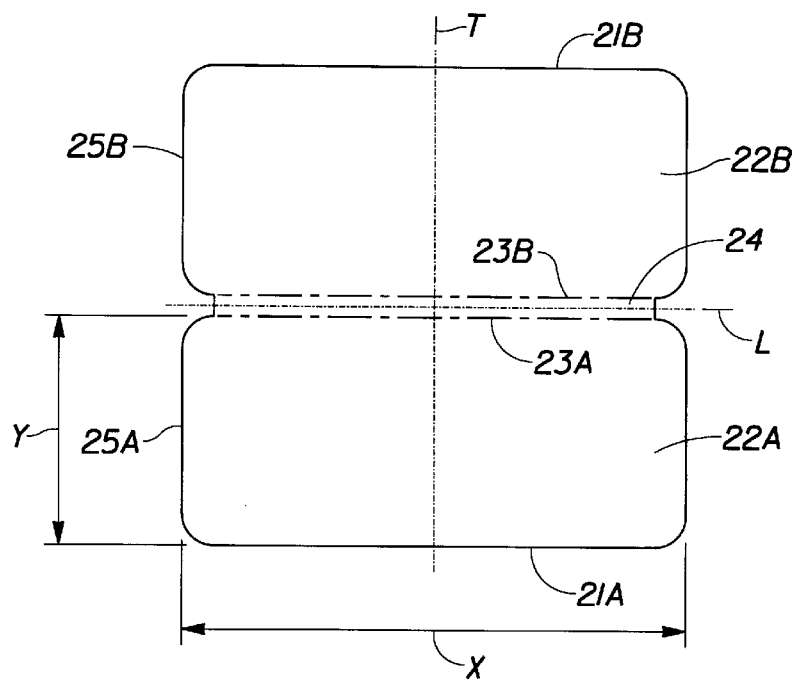
FIG. 1 is a plan view of a preferred interlabial absorbent structure embodiment of the present invention shown fully flat out with the body contacting surface thereof facing the viewer.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the interlabial absorbent structure 20 shown in FIG. 1. As used herein, the term "interlabial absorbent structure" describes an absorbent article which resides at least partially within a wearer's interlabial space. As used herein the term "interlabial space" refers to the that space in the pudendal region of the female anatomy which is located between the inside surfaces of the labia majora extending into the vestibule. Located within this interlabial space are the labia minora, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of their labia majora and labial minora. For purposes of the present description, however, such differences need not be specifically addressed. It will be recognized that the disposition of the interlabial structure into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy,* Running Press 1901 Ed. (1974), at 1025–1027.

As used herein, the term "pudendal" refers to the externally visible female genitalia.

General Description of the Interlabial Absorbent Structure of the Present Invention The interlabial absorbent structure 20 shown in FIG. 1, at least partially, blocks and absorbs and more preferably completely blocks, intercepts, and absorbs the flow of menses, urine, and other bodily exudates from a wearer's vaginal introitus and urethra. The interlabial absorbent structure 20 should be of a suitable size and shape that allows at least a portion thereof to fit comfortably within the wearer's interlabial space and to cover the vaginal introitus, and, preferably, also the wearer's urethra. The interlabial absorbent structure 20 is, at least partially, held in place by exerting a slight laterally outwardly-oriented pressure on the walls of a wearer's interlabial space and by the capillary forces between the panels 22 thereof and the naturally moist walls of the interlabial space. The interlabial absorbent structure 20 of the present invention can be worn as a "stand alone" product. Alternatively, it can be worn as a back up to a tampon or in combination with a sanitary napkin, a pantiliner, or incontinence pad for menstrual or incontinence use. The Interlabial absorbent structure 20 can be worn with conventional panties or it can be used with menstrual shorts.

As is shown in FIG. 1, the interlabial absorbent structure 20 has two centerlines, a longitudinal centerline L and a transverse centerline T. The term "longitudinal", as used herein, refers to a line, axis or direction in the plane of the interlabial absorbent structure 20 that is generally aligned with (e.g., approximately parallel to) a vertical plane which bisects a standing wearer into left and right body halves when the interlabial absorbent structure 20 is worn. The terms "transverse" or "lateral" as used herein, are interchangeable, and refer to a line, axis or direction which lies within the plane of the interlabial absorbent structure 20 that is generally perpendicular to the longitudinal direction.

The interlabial absorbent structure 20 also has a body surface 20T, which contacts the walls of a wearer's interlabial space, and an opposed rear surface 20R. The body and rear surfaces of other elements of the present invention will be described in a similar manner with a "T" being appended to the reference number of the element to designate the body surface thereof and a "R" being appended to designate the rear surface thereof.

The present invention is directed to an interlabial absorbent structure. FIG. 1 is a plan view of the interlabial absorbent structure 20 showing a preferred embodiment of the present invention. As shown in FIG. 1, the interlabial absorbent structure 20 preferably comprises a pair of laterally opposed panels 22A and 22B. (Similar nomenclature will be used with respect to other elements comprising the panels. That is, the letters A and B will be appended to the reference numbers for the various elements of a panel whenever it is necessary or advantageous to relate an element to a specific panel.) The panels 22A, 22B are connected by a narrow isthmus 24.

Although other shapes, such as oval, trapezoidal, irregular (e.g. butterfly), and the like, are suitable, each panel preferably has an approximately rectangular configuration (rounded rectangular). Each panel has a distal longitudinal side edge 21, a proximal longitudinal side edge 23, and a pair of transversely extending end edges 25, the end edges 25, the distal edge 21, and the proximal edge 23 defining a periphery for each panel 22. The panels 22 also have a longitudinal length X and a transverse width Y.

The interlabial absorbent structure 20 of the present invention further comprises an isthmus 24 which connects the panels 22A, 22B. The isthmus 24 also comprises at least one fold line so the interlabial absorbent structure is able to better conform to the complex anatomy of a wearer's interlabial space. The isthmus 24 is the portion of the interlabial absorbent structure that is positioned furthest inward into a wearer's interlabial space. The isthmus 24 also preferably directs any bodily fluids that may be deposited thereon in a longitudinal direction. Each of these components is discussed in greater detail in the following sections.

The interlabial absorbent structure 20 may optionally further comprise extraction means (not shown), such as a string, a loop, a tab, or the like, to aid in the removal of a soiled device. Such extraction means would be attached to the rear surface 20R (i.e., the surface opposite the body surface 20T of the interlabial absorbent structure 20) and would extend at least partially outside a wearer's labia majora.

A tab may also serve as an insertion aid by providing a stiffened member for gripping, so a wearer's fingers are protected from soiling by the panels 22 when the interlabial absorbent structure 20 is inserted. Such an insertion tab may have a dimension in the longitudinal direction of between about 0.8 inches (20 mm) and about 3.0 inches (76 mm) and a caliper of less than 0.12 inches (3 mm). The tab may have a length of between about 0.4 inches (10 mm) and about 2.4 inches (60 mm), preferably, between about 0.6 inches (15 mm) and about 1.6 inches (40 mm). It should be stiff enough so it is easily grasped by a wearer's fingers as the interlabial absorbent structure 20 is inserted into her interlabial space. The tab should also be sufficiently flexible to accommodate the deformation of the interlabial space caused by a sitting position so as not to be a source of discomfort.

The interlabial absorbent structure 20 also preferably breaks up into a plurality of small fragments when the structure 20 is exposed to water and mild agitation. For example, a soiled interlabial absorbent structure 20 preferably breaks up into at least two fragments when it is deposited into a conventional toilet and exposed to the relatively mild agitation caused by flushing and passage through a typical household sewage system.

Still more preferably, the interlabial absorbent structure comprises biodegradable components. As used herein, the term "biodegradable component" is intended to describe a material having greater than about 70% biodegradation (percentage of theoretical carbon dioxide evolution) after 28 days when measured according to the Modified Sturm Test which has been designated Method 301B by the Organization for Economic Cooperation and Development. Preferably, the materials comprising the present invention have a biodegradation greater than about 80% and, more preferably, biodegradation is greater than about 90%.

The Panels

Since the panels 22A, 22B preferably mirror each other, the structure of a single panel 22 will be described with the understanding that the same structure is preferably repeated in the opposing panel. Each panel 22 contacts the walls of a wearer's interlabial space helping to maintain the interlabial absorbent structure 20 in a desired position throughout a wide range of wearer movements and also minimizing leakage of bodily fluids around the interlabial absorbent structure 20. The panels 22 also provide absorbent capacity to the interlabial absorbent structure 20 for storing such bodily fluids. The structure of a panel 22 is shown most clearly in FIG. 2. As can be seen therein, a panel 22 comprises a plurality of individual plies 26. such plies can be provided, for example, by folding a web of material into a plurality of pleats or by disposing sheets of material on top of each other and joining the sheets along at least one edge thereof Preferably, the plies 26 are formed by folding a web of material into a plurality of pleats.

A panel 22 may comprise any absorbent means which is capable of absorbing or retaining liquids (e.g., menses and/or urine). A panel 22 may be manufactured from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers (e. g. rayon); synthetic fibers such as polyester fibers, including crimped fibers and fibers having channels of capillary dimension provided thereto by the extrusion process; peat moss including combinations of peat moss and other materials; tissue including tissue wraps and tissue laminates; absorbent foams (both blown foams and high internal phase emulsion (HIPE) foams); absorbent sponges; superabsorbent polymers; absorbent gelling materials; or any equivalent material or combinations of materials, or mixtures of these. Preferred absorbent materials comprise: tissue webs (air laid and wet laid webs are both suitable); webs of woven materials, nonwoven webs (e.g. carded webs, spun bonded webs, melt blown webs, and the like); and thin layers of foam. In the preferred embodiment shown in FIGS. 1 and 2 each panel 22 comprises a folded web of tissue.

The preferred tissue web preferably is provided with a temporary wet strength additive to enable the tissue web to resist loss of strength due to absorbed liquids which can cause the interlabial absorbent structure 20 to shred and bunch as it is exposed to wearer movement. The level of the temporary wet strength additive should be high enough such that the absorbent structure 20 resists shredding and bunching but not so high that the interlabial absorbent structure 20 fails to "break apart" in a domestic plumbing system (interlabial absorbent articles are frequently disposed of by flushing them down a toilet). The interlabial absorbent structure 20 of the present invention will be dispersed into at least two fragments within about 120 minutes of being placed into mildly agitated room temperature water as described in the TEST METHODS section below. Preferably, the disposable interlabial absorbent structure 20 will be dispersed into a plurality of small fragments within about 30 minutes of being placed into mildly agitated room temperature water, more preferably, within about 15 minutes of being exposed to such mildly agitated room temperature water. Suitable temporary wet strength additives are the glyoxalated polyacrylamide resins available from Cytec Industries Inc. of Stanford, CT under the designation Parez™. Particularly preferred is Parez™ 631 NC. When Parez™ 631 NC is used at a level between about 0.5% and about 1.0% in the wet laid apertured tissue, the interlabial absorbent structure 20 has a satisfactory balance of mechanical integrity during use and dispersibility during disposal.

Wet burst strength has also been used by the art as a measure of the sensitivity of a tissue paper to water exposure. Preferably, the wet strength additive provides the tissue web with a wet burst strength of between about 15 grams and about 200 grams. More preferably the wet burst strength is between about 15 grams and about 50 grams. A method for measuring wet burst strength is described in the TEST METHODS section below.

Suitable tissue webs comprise at least 50% cellulosic fibers and have a basis weight between about 10 grams per square meter and about 60 grams per square meter. Such tissue webs can be produced using wet papermaking techniques as are known to the art or using air laying techniques as are also known to the art. Such tissue webs can also further comprise thermoplastic fibers which when melted provide strength and resiliency to the web. Webs comprising at least 90% cellulose fibers are preferred. Particularly preferred tissue materials comprise a wet laid tissue having a basis weight of about 35 pounds per 3000 square feet (58 grams per square meter) which is available from Fort Howard Corp. of Green Bay, Wis. or the wet laid tissue having a basis weight of about 18 pounds per 3000 square feet (30 grams per square meter) which is available from the Procter & Gamble Company as CHARMIN bathroom tissue.

As noted above and shown in FIG. 2, the preferred structure of a panel 22 is provided by folding a web of tissue into a plurality of pleats to create the plies 26. As can also be seen in FIG. 2, the plies 26 are arranged in a laterally side by side relationship. The tissue web can be folded so that it has any suitable number of plies 26. Preferably the number of plies 26 is sufficient to provide the requisite absorbent capacity to the interlabial absorbent structure 20 (unless auxiliary capacity in the form of a superabsorbent polymer or the like is provided) yet not so large so as to cause wearer discomfort. Preferably, the web of tissue is folded so that the dry caliper of the interlabial absorbent structure 20 is less than about 7 millimeters, more preferably less than about 5.5 millimeters, still more preferably less than about 4.5 millimeters. The number of plies 26 provided to each panel 22 by such folding will depend on the caliper of the web of tissue that is being folded. A method for measuring dry caliper is provided in the TEST METHODS section below.

The plies 26 are preferably connected or joined at at least one of their distal edges 21 or their proximal edges 23 in some suitable manner to insure the panels 22 remain in a folded configuration and do not unfold. The plies 26 can be joined by a variety of means including folding, pressure bonding (crimping), adhesive means, stitching (e.g. with cotton or rayon thread), and thermal bonding (if the tissue web also comprises thermoplastic binder fibers). Preferably the plies are joined by folding the web of tissue into a plurality of pleats so that the plies 26 are at least partially joined at their distal edges 21 and joining the plies 26 at the proximal edges 23 to define the isthmus 24 using means known to the art. Stitching is particularly preferred for joining the plies 26 at the proximal edges 23.

Each panel 22 should be of a suitable size and shape so that the interlabial absorbent structure 20 fits comfortably within a wearer's interlabial space. That is, each panel 22 should be sized so that the panel covers the "direct line of sight" from the distal edge of a wearer's labia majora to her vaginal introitus. As noted above, a panel 22 preferably has a rounded rectangular shape as is shown in FIG. 1. Preferably, each panel 22 has a surface area of between about 8 square centimeters and about 65 square centimeters. More preferably the surface area of each panel 22 is between about 10 square centimeters and about 35 square centimeters. Said another way, each panel 22 may have an "X" dimension between about 2 inches (5 centimeters) and about 6 inches (15 centimeters) and a "Y" dimension between about 0.6 inch (1.5 centimeters) and about 2 inches (5 centimeters).

The thickness or caliper of each panel 22 is also of significance with respect to the comfort experienced when wearing the interlabial absorbent structure 20 and to the absorbent capacity of the interlabial absorbent structure 20. As noted above, the caliper should be sufficient to provide the requisite absorbent capacity to the interlabial absorbent structure 20 yet not so large so as to cause wearer discomfort. Preferably, the caliper of each panel 22 is between about 1 millimeter and about 3.5 millimeters, preferably between about 1.5 and 3 millimeters. More preferably, the caliper of each panel 22 is between about 1.5 and 2.5 millimeters.

Figure 2:
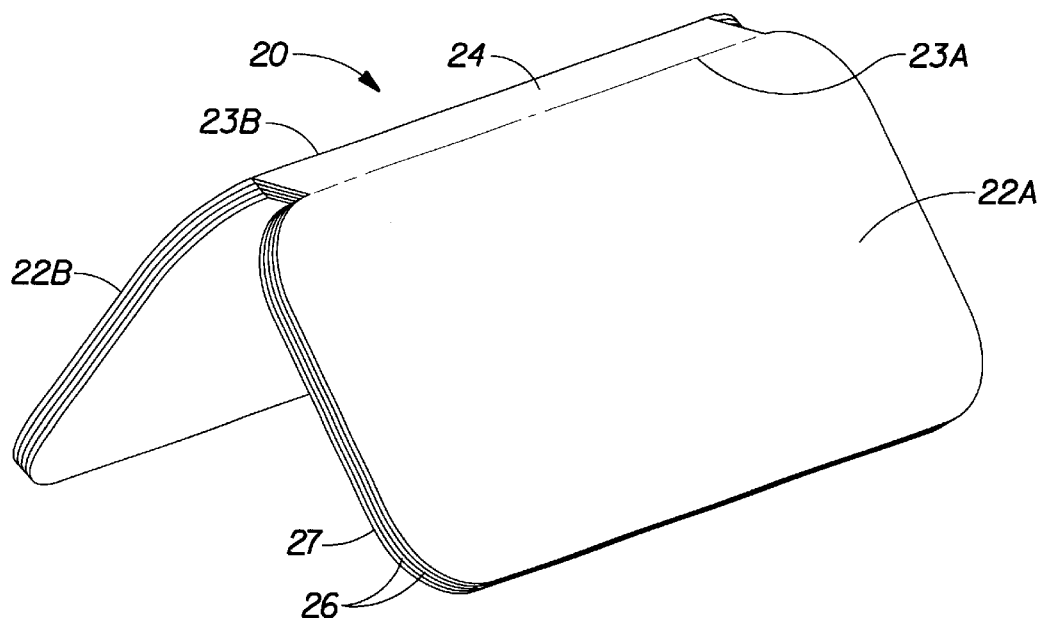
FIG. 2 is a perspective view of the interlabial absorbent structure of the present invention in a folded configuration ready for insertion into a wearer's interlabial space.

When the interlabial absorbent structure 20 is folded for use as shown in FIG. 2 and fully saturated with 0.9% aqueous saline solution the caliper should be less than about 15 millimeters, preferably less than about 6 millimeters and more preferably less than about 4 millimeters under a confining pressure of 0.25 psi (1.7 kPa). A method for measuring wet and dry caliper is provided in the TEST METHODS section below.

The interlabial absorbent structure is preferably provided with sufficient absorbency to absorb and retain exudates discharged from a wearer's body. The absorbent capacity is controlled by the number and the composition of the individual plies 26, the volume of the interlabial absorbent structure 20 and the presence (or absence) of superabsorbent polymers, absorbent gelling materials, or the like. Depending on the specific structure chosen for a panel 22, the panel can have an absorbent capacity for 0.9% aqueous saline solution of between about 1 gram and about 30 grams. Preferably the absorbent capacity is between about 1 gram and about 15 grams, more preferably between about 2 grams and about 10 grams, of 0.9% aqueous saline solution. A method for measuring absorbent capacity is given in the TEST METHODS section below.

Each panel 22 is also preferably sufficiently flexible so as to conform to the convoluted surface of a wearer's interlabial space. Such flexibility also allows the interlabial absorbent structure to respond to wearer movements without exerting a noticeable force on her body (i. e. high flexibility increases wearer comfort). Such flexibility can be characterized as follows. If the panels have a stiffness less than the stiffness of a single sheet of bathroom tissue, such as CHARMIN, they are too flexible and the risk of bunching during wear is unacceptably high. If the panels have a stiffness similar to the stiffness of a sheet of conventional typing paper, they are too stiff and the panels would be unable to conform to the convolutions of the walls of the interlabial space and respond to wearer movements.

In an alternative embodiment (not shown), each panel 22 may be provided with a plurality of preferential lines of bending to accommodate the non symmetric spreading of the labia during certain motions, such as those when one leg is thrust to the side or an asymmetric squatting motion. Furthermore, such a plurality of preferential bend lines is also advantageous because the walls of the interlabial space may not be symmetric-often, one lip of the labia minora or the labia majora is longer than the other.

In one preferred embodiment of the present invention, the inner ply 27 of each panel 22 comprises a tissue having greater wet burst strength than the wet strength of the remaining plies 26. Since a wearer's fingers are most likely to contact the inner ply 27 when inserting and removing the interlabial absorbent product 20, this greater burst strength provides additional resistance to "poke through", particularly when the interlabial absorbent structure 20 is wet with absorbed bodily fluids, without substantially affecting other properties. Such resistance can provide a wearer with additional confidence that her hands will not become unacceptably soiled when inserting or removing the interlabial absorbent structure 20. Suitable tissue materials have a wet burst strength that at least about 30 grams and at least twice the wet burst strength of the tissue comprising the plies 26, preferably the wet burst strength of the inner ply 27 is greater than about 50 grams. A suitable tissue has a basis weight of about 14 pounds per 3000 square feet, comprises the level of temporary wet strength additive required to provide the desired wet burst strength, and can be made using the methods described in U.S. Pat. No. 3, 301,746, issued to Sanford, et al. on Jan. 31, 1967.

Since the inner ply 27 of this preferred embodiment comprises a different material than the remaining plies 26, it can be joined to the remaining plies 26 using means known to those skilled in the art. For example, the inner ply 27 can be joined to the remaining plies 26 using a bead of adhesive (not shown) or other such means as may be known for joining two plies of material.

Optional Panel Components

If desired, each panel 22 can also comprise other optional components. For example, each panel could comprise a topsheet as its body contacting surface 22T and/or a backsheet as its rear surface 22R. If the interlabial absorbent structure 20 also comprises a topsheet and a backsheet, the topsheet and the backsheet are preferably joined to each other along the distal edge 23 and the end edges 25 of each panel 22.

The topsheet is compliant, soft feeling, and non-irritating to the wearer's skin. Further, the topsheet is liquid pervious permitting liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A particularly preferred nonwoven material for use as a topsheet comprises a hydrophilic, spun bonded material having a basis weight of about 0.68 ounces per square yard (23 grams per square meter) such as is supplied by Corovin GmbH of Penne, Germany as Corolind H23GSM.

The body surface of the topsheet is preferably hydrophilic so as to help liquid to transfer through the topsheet faster than if the body surface was not hydrophilic so as to diminish the likelihood that menstrual fluid will flow off the topsheet rather than flowing into and being absorbed by the absorbent core. For example, surfactant may be incorporated into the polymeric materials of a formed film topsheet such as is described in U.S. patent application Ser. No. 07/794, 745, filed on Nov. 19, 1991 by Aziz, et al., the disclosure of which is incorporated herein by reference. Alternatively, the body surface of the topsheet can be made hydrophilic by treating it with a surfactant such as is described in U.S. Pat. No. 4,950,264 issued to Osborn on Aug. 21, 1990, the disclosure of which is incorporated herein by reference.

The backsheet is preferably impervious to bodily fluids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet provides extra protection to a wearer against soiling her hands when inserting or removing an interlabial absorbent structure 20 of the present invention. The backsheet may thus comprise a woven or nonwoven material, polymeric films such as thermoplastic films of polyethylene or polypropylene, or composite materials such as a film-coated nonwoven material. For example, the backsheet can comprise a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. More preferably, the backsheet comprises a tissue web impregnated with a resin so as to cause the tissue web to be water resistant. Such water resistant tissue webs can be produced according to the process described in U.S. Pat. No. 5,558, 344, issued in the name of Ahr, et al. on Nov. 26, 1996, the disclosure of which is incorporated herein by reference.

The Isthmus

As noted above, the interlabial absorbent structure 20 comprises two panels 22A, 22B which are joined by an isthmus 24. The isthmus 24 joins the panels 22A, 22B and provides a preferential fold line for forming the interlabial absorbent structure 20 into a configuration suitable for use. Preferably, the isthmus 24 also provides means for longitudinally directing any fluids that may be deposited thereon.

The isthmus 24 can comprise an extension of the material comprising the panels 22A, 22B or it can comprise a separate element to which the panels 22a, 22B are joined. Preferably, the isthmus comprises an extension of the material comprising the panels 22A, 22B.

In its simplest execution, the isthmus is merely a region between the panels 22A and 22B when the panels are folded. As noted above, the panels 22 preferably have a rounded rectangular configuration. This means that the isthmus 24 would comprise the proximal edges 23A, 23B of the panels 22A, 22B in this simplest execution. Preferably, the isthmus 24 is defined by preferential fold lines which define the proximal edges 23A, 23B as is shown in FIGS. 1 and 2.

Preferably, however, the isthmus 24 has a measurable length (preferably slightly shorter than the length X of the panels 22) and a width which can be defined as the lateral distance between the proximal edges 23A, 23B of the panels 22. The lateral distance between the proximal edges 23A, 23B is between about 1 millimeter and about 7 millimeters. Preferably, this lateral distance is between about 2 millimeters and about 6 millimeters. More preferably, the distance is between about 3 millimeters and about 5 millimeters. One skilled in the art will recognize that this lateral distance may be somewhat greater than the combined caliper of the two panels 22A, 22B which comprise the preferred embodiment of the present invention.

Figure 3:
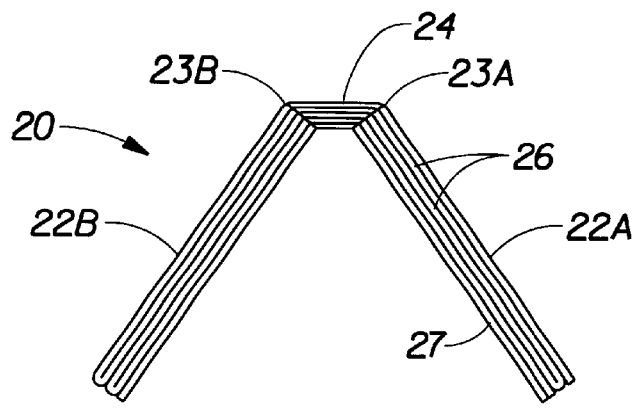
FIG. 3 is an end view an alternative embodiment of the interlabial absorbent structure of the present invention.
Figure 4:
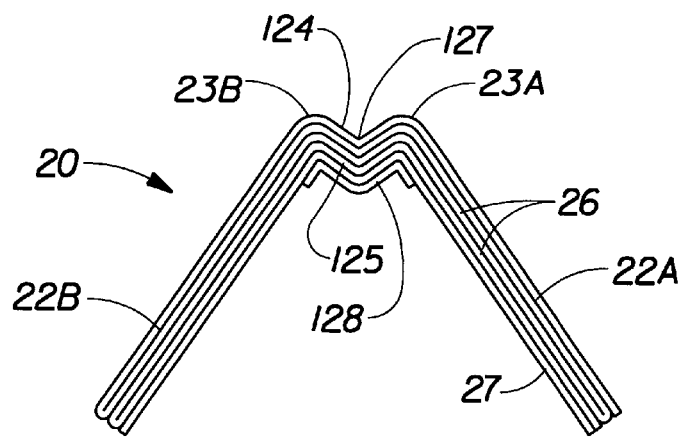
FIG. 4 is an end view of the interlabial absorbent structure of the present invention showing a second alternative embodiment of the invention.
Figure 5:
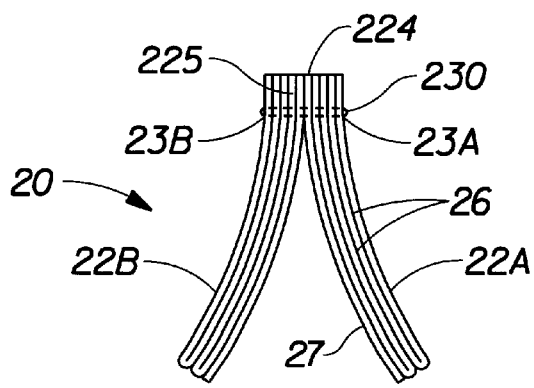
FIG. 5 is an end view of the interlabial absorbent structure of the present invention showing a third alternative embodiment of the present invention.

The Applicants have found that the walls of the interlabial space are surprisingly insensitive, except for the portion nearest the external surface of the labia majora and the transition zone between the interlabial space and the vagina (i. e. the hymenal ring). This means any portion of the interlabial absorbent structure 20 that, when the structure is worn, lies in these relatively insensitive portions can have a surprisingly large caliper. Said another way, the isthmus 24, as mentioned above, may have a caliper (lateral distance) that is larger than the caliper of the panels (a portion of the panels may extend outside the interlabial space placing that portion in the sensitive region of the interlabial space). as a result, the isthmus 24 may be designed to provide additional performance benefits to the interlabial absorbent structure 20 by taking advantage of this "extra" caliper. FIGS. 3–5 show end views of interlabial absorbent structures having several alternative embodiments of the isthmus 24. Each of these embodiments provides additional performance benefits to the interlabial absorbent structure 20. they will be discussed individually below.

In FIG. 3 the isthmus 24 comprises a compression zone where the portion of the interlabial absorbent structure 20 lying between the proximal edges 23A, 23B of the panels 22A, 22B (i.e. the isthmus 24) has been compressed to provide a compression zone to encourage longitudinal distribution of bodily fluids that are deposited on the interlabial absorbent structure 20. As is noted above, the isthmus 24 is that portion of the interlabial absorbent structure 20 that is positioned furthest into a wearer's interlabial space. Therefore, it will be the first portion of the interlabial absorbent structure 20 to intercept bodily fluids that are released by the vaginal introitus or by the urethra. Thus, bodily fluids deposited on the isthmus 24 will be encouraged to flow along the isthmus by the compression zone making more complete use of the absorbent capacity of the panels 22A, 22B.

If desired, the isthmus 24 of this embodiment can comprise alternating regions of lower and higher density (not shown). This would provide the additional advantage of increased acquisition rate in the lower density zones (i.e. having a density similar to the panels 22) and the flow along the isthmus 24 when an acquisition zone becomes saturated in the higher density zones (i.e. having the compressed density discussed above).

Compressing the region between the proximal edges 23A, 23B so the isthmus 24 comprises a compression zone can be done using means known to the art. For example, the portion of the interlabial absorbent structure 20 comprising the isthmus 24 could be caused to pass through a nip increasing the density thereof while the remainder of the interlabial absorbent structure 20 is not densified. While the density in the compression zone would be increased by such a processing step, it should not be increased so much that the rate of absorbency becomes unacceptably low (it is well known that absorbency rate and density have an inverse relationship for fibrous structures such as the preferred multiply tissue structure of the present invention). It has been found that a density similar to the density of the channels in ALWAYS Sanitary Napkins with Channels which are available from the Procter & Gamble company, Cincinnati, Ohio provides a satisfactory balance between longitudinal fluid direction and absorbency rate.

A second alternative embodiment of the isthmus 124 is shown in FIG. 4. In this case, the portion of the interlabial absorbent structure 20 that lies between the proximal edges 23A, 23B has been folded so that the isthmus 124 takes on a "V" shape. This "V" shape provides a channel 127 for longitudinally directing bodily fluids that may be disposed on the isthmus 24. One of skill in the art will recognize that a "V" shape is not the only shape that will provide a channel suitable for longitudinal direction of bodily fluids. A non-limiting list of other suitable shapes includes: semicircular, "U" shaped, and any other shape capable of forming a continuous channel that is open at the top. The "V" shape is preferred because the forming thereof using conventional folding techniques is straightforward. Preferably, the isthmus 124 further comprises a resilient member 128 that is disposed beneath the fibrous portion 125 of the isthmus 124 as is also shown in FIG. 4.

The "V" shaped channel 127 of the alternative embodiment of the isthmus 124 shown in FIG. 4 distributes deposited bodily fluids in the longitudinal direction in a similar manner to that described above. Such a folded structure has the additional advantage of having a more rapid acquisition rate than the compression zone embodiment shown in FIG. 3. This improved acquisition rate is due to the fact that the fibrous tissue structure of the preferred embodiment of the interlabial absorbent structure 20 as is described above is not densified. Rather the capillaries thereof are more open with a resulting increase in acquisition rate.

Preferably the isthmus 124 further comprises a "M" shaped resilient member 128 disposed beneath the fibrous portion 125 as is shown in FIG. 4. The resilient member 128 serves two purposes: 1) the resilient member 128 serves to resist the compressive forces due to a wearer's labia which would tend to close off the channel 127 and 2) the legs of the "M" serve to spread the panels 22A, 22B apart with resulting improved contact with the walls of the interlabial space.

The resilient member 128 needs to be stiff enough to resist complete closure of the channel 127 (i.e. have sufficient compression resistance) yet not be so stiff so as to become a source of wearer discomfort. Examples of some suitable nonabsorbent materials which may be placed under the fibrous portion 125 include thermoplastic polyethylene, polypropylene, synthetic foams, films or nonwoven materials having the requisite compression resistance. One exemplary foam material for use as the resilient member 128 is a radiation crosslinked, closed cell polyethylene foam known as VOLARA 2A obtained from Voltek Corp., Lawrence, Mass.

The "V" shaped configuration of the embodiment of the isthmus 124 that is shown in FIG. 4 can be formed by the following method: 1) providing a resilient member 128 that has been preformed into an "M" shape, 2) providing an attachment means (not shown) for joining the resilient member 128 to the fibrous portion 125 to the upper surface of the resilient member, 3) disposing the resilient member 128 along the longitudinal centerline L and adjacent the lower surface of the fibrous portion 125, and 4) depressing the fibrous portion 125 so that the lower surface thereof contacts the attachment means which joins the fibrous portion 125 to the resilient member 128 and causes the isthmus 124 to assume a "V" configuration.

A third embodiment of the isthmus is shown as 224 in FIG. 5. In this embodiment the plies 26 extend a distance "Z" beyond the proximal edges 23A, 23B of the panels 22. The panels 22A, 22B are joined at their proximal edges 23A, 23B by a plurality of discrete securement means 230. As one of skill in the art will recognize, the space between the extended portion of the plies 26 encourages longitudinal distribution of bodily fluids that are deposited on the isthmus 224. Also, since the securement means 230 are spaced apart, the structure shown in FIG. 5 provides a pathway for such deposited fluids to flow into the volume between the plies 26 in the panels 22A, 22B (As was discussed above, the void volume between the plies 26 provides capacity for absorption of cellular debris, blood clots, and the like that which would otherwise clog capillaries within the individual plies of tissue.

This embodiment of the isthmus which is described above and shown as 224 in FIG. 5 comprises an extended portion 225 of the material comprising the panels 22. The portion 225 extends a distance "Z" beyond the proximal edges 23A, 23B of the panels 22 to create the isthmus 224. As will be recognized, the distance "Z" is important in that: 1) if "Z" is too short, the isthmus 224 will be difficult to fabricate or 2) if "Z" is too large, the extended portion 225 will have a tendency to fold over which could block the pathway to the void volume between the plies 26. Difficulty of insertion may also be increased if "Z" is too large. Preferably "Z" is between about 1 millimeter and about 5 millimeters. More preferably, "Z" is between about 1 millimeter and about 3 millimeters.

The "Z" dimension, in combination with the properties of the material which comprises the plies 26, also defines the compression stiffness of the isthmus 224. The stiffness of the isthmus 224 will affect the wearing comfort of the interlabial absorbent structure 20. The compression stiffness should be less than or equal to about 500 grams. Preferably, the compression stiffness is less than about 300 grams and more preferably less than or equal to about 200 grams. A method for compression stiffness is given in the TEST METHODS section below.

The panels 22A, 22B are joined at a their proximal edges 23A, 23B using a plurality of discrete securement means 230 to form the isthmus 224. The discrete securement means 230 can comprise any means known to the art to join the panels 22A, 22B at a plurality of spaced apart locations along the proximal edges 23 thereof. For example, the panels could be joined using stitching (e. g. with cotton or rayon thread), thermal bonds (if the plies comprise a thermoplastic material), spots of adhesive, or any other such securement means as is known to the art. Preferably the panels 22A, 22B are joined by stitching them together.

To use the interlabial absorbent structure of the present invention a wearer would fold the structure along its longitudinal centerline L so it assumes a configuration similar to that shown in FIG. 2. She would grasp the structure adjacent the distal edges 21A, 21B thereof, spread her labia and insert the structure such that the isthmus 24 is in close proximity to her pelvic floor. When she releases the distal edges 21A, 21B, her labia will close around the interlabial absorbent structure 20 holding it in place. As discussed above, the panels 22A, 22B will conform to and remain in contact with the walls of the wearer's interlabial space throughout a wide range of wearer motions.

Test Methods

Burst Strength

Overview

The test specimen, held between annular clamps, is subjected to increasing force that is applied by a 0.625 inch diameter, polished stainless steel ball. The burst strength is that force that causes the sample to fail. Burst strength may be measured on wet or dry samples.

Apparatus

| | |
|---|---|
| Burst Tester | Intelect-II-STD Tensile Test Instrument, Cat. No. 1451-24PGB or the Thwing-Albert Burst Tester are both suitable. Both instruments are available from Thwing-Albert Instrument Co., Philadelphia, PA. The instruments must be equipped with a 2000 g load cell and, if wet burst measurements are to be made, the instruments must be equipped with a load cell shield and a front panel water shield. |
| Conditioned Room | Temperature and humidity should be controlled to remain within the following limits: Temperature: 73 ± 3° F. (23° C. ± 2° C.) Humidity: 50 ± 2% Relative Humidity |
| Paper Cutter | Scissors or other equivalent may be used |
| Pan | For soaking wet burst samples, suitable to sample size |
| Solution | Water for soaking wet burst samples should be equilibrated to the temperature of the conditioned room. |
| Timer | Appropriate for measuring soak time |

Sample Preparation

1) Cut the sample to a size appropriate for testing (minimum sample size 4.5 in×4.5 in). Prepare a minimum of five samples for each condition to be tested.
2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute
   Break Sensitivity: 20 grams
   Peak Load: 2000 grams
2) Calibrate the load cell according to the expected burst strength.

Measurement and Reporting

1) Operate the burst tester according to the manufacturer's instructions to obtain a burst strength measurement for each sample.
2) Record the burst strength for each sample and calculate an average and a standard deviation for the burst strength for each condition.
3) Report the average and standard deviation for each condition to the nearest gram.

Report the average and the standard deviation for each group of four samples.

Dry Caliper

Principle

Dry caliper of a sample can be determined using a comparator gauge that is weighted to provide a predetermined confining pressure.

Apparatus

A suitable comparator gauge gage is the Ames, Model 130 with dial indicator Model 482, available from the B. C. Ames, Company of Waltham, Mass. The comparator gauge should have a circular comparator foot made of aluminum capable of exerting a loading pressure of 0.25 pounds per square inch (1.7 kPa). It will be recoginzed that the diameter of the comparator foot can be varied to accommodate different sample sizes as long as the loading pressure remains constant.

Operation

1. The comparator gauge is zeroed according to the manufacturer's instructions.
2. The comparator foot is raised and the sample is placed on the base plate. The sample is positioned on the base plate so that when the foot is lowered it is in the center of the sample. The comparator foot should be at least 5 millimeters from all sample edges. Try to smooth out or avoid any wrinkles in the sample.
3. Gently lower the foot onto the sample.
4. Determine caliper by reading the comparator dial 30 seconds after the foot comes in contact with the sample.
5. Repeat steps 2 through 4 for an additional 2 samples.

Calculations

The average of the three readings is the caliper of the material.

Wet Caliper

Principle

The thickness or caliper of a product may be determined using a motor-operated micrometer which measures the perpendicular distance between the two principle surfaces of the product under prescribed conditions. Using this equipment, measurements are made and reported to the nearest 0.1 milillimeter.

Apparatus

| | |
|---|---|
| Blotter Paper or Absorbent Towel | Clean, dry |
| Conditioned Room | Temperature and humidity controlled within the following limits: Temperature: 73 ± 2° F. Relative Humidity: 50 ± 2% |

| | -continued |
|---|---|
| Flat Pan for Immersing Sample | Pan to be larger than the largest sample by at least 100%. |
| Timer | Digital Stopwatch |
| Micrometer | A suitable micrometer is Model 89-11 Electronic Thickness Tester which is available from the Thwing-Albert Instrument Co., Philadelphia, PA. The sample load should be 0.25 pounds per square inch (1.7 kPa). |
| Scissors | Office shears, 7 in. cut length or equivalent. |
| Solution | Aqueous saline solution (0.9%) at the temperature of the conditioned room used. |

General Practices

The following general practices should be followed.
1. Set up and calibrate the micrometer as described in the manufacturer's instructions.
2. Do not use sample portions cut with a die if more sample is available. Some compression of paper takes place during sample cutting in a die which can cause results to be low.
3. Do not make micrometer readings on creases resulting from folds.
4. Do not make micrometer readings on paper with obvious defects such as wrinkles, tears, holes, etc. If the sample portions selected have defects of this kind, making them unsuitable for testing, discard. Replace with another sample portion which is free of such defects, selecting the replacement sample portion from the same layer or area in the sample. In general, select portions for testing not designated for other tests.
5. Keep handling of the surface area of the sample portions to a minimum. Touch only the edges when possible.
6. Do not test the same area of a sample portion more than once; the pressure of the anvil may cause changes in caliper.
7. Do not allow the instrument cycle to force you to make readings at a pace too fast for proper attention to correct procedure.
8. Upon completion of testing, always turn off the micrometer with the pressure foot down in contact with the anvil.

Sample Preparation

Obtain at least three samples and take the micrometer reading in the center of each sample.

Sample Conditioning

None required.

Pre-measurement Technique

Turn on the motor to the micrometer then adjust the zero setting of the micrometer according to the manufacturer's instructions before analyzing each sample portion or series of sample portions.

Immediately prior to measurement, lower the sample into a shallow pan of the saline solution such that the sample can be completely submerged.

Immediately upon completion of wetting, start the stop watch and allow the sample to remain submerged for 10 minutes. Remove the sample from the saline solution using both hands and grasping at the two sides adjacent along a longitudinal line (sample hangs vertically in transverse direction). Quickly let the sample drain while holding nearly in this vertical plane but touching the lower edge to a dry absorbent surface (e.g. BOUNTY paper towels). Drain for 30 seconds and begin the measurement as is described below.

Operation

Turn on the motor to the micrometer, then adjust the zero on the micrometer as described in the manufacturer's instructions analyzing each sample portion or series of sample portions.

When the foot is in the up position, place the sample portion on the micrometer anvil. The sample portion must be located carefully on the anvil so that when the foot comes down, it will be at least 0.50 inches (1.27 cm) from the edges of the sample portion. Read the panel meter of the micrometer to the nearest 0.1 millimeter when the foot is in the down position near the end of the dwell time. Report the micrometer reading to the nearest 0.1 millimeter. Continue in this manner for each sample portion.

Watch the zero setting. In the event the panel meter momentarily reads 0.1 mililimeter or more away from zero, stop testing. Clean the surface areas of the foot and anvil and rezero the micrometer.

At the completion of the test, if a Thwing-Albert instrument is used, turn the instrument to the "STAND-BY" position with the foot down all the way against the anvil before turning the main power switch off.

Calculations

Calculate the average and standard deviation of the micrometer readings for each sample and report the average caliper for each sample to the nearest 0.1 mililimeter.

Absorbent Capacity

Absorbent capacity may be determined as follows. The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out to the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the absorbent capacity of the article.

Compression Stiffness

Apparatus

| | |
|---|---|
| Tensile/ Compression Tester | This test requires a constant rate tensile and compression testing apparatus such as an INSTRON Model 4502 tensile and compression testing machine, which is available from Instron Corporation of Canton, MA. |
| Load Cell | Ten Newton compression load cell suitable for use with tensile/compression tester. |
| T-Rod | The T-rod comprises a pair of 6.40 mm diameter metal rods perpendicularly mounted together in a T configuration. The drive rod (the longer of the rods) is about 125 mm long and the push rod (the shorter of the rods) is about 75 mm long. Preferably, the end of the drive rod is tapered to fit the circumference of the push rod and the two are glued, welded and/or screwed to each other. The opposite end of the drive rod is mounted to the crosshead unit of the |

-continued

| | |
|---|---|
| | tensile/compression tester. |
| Sample Clamp | Adjustable clamp having opposed vertical faces and a horizontal top surface. |

Procedure
1. Set up tensile/compression tester according to manufacturer's instructions.
2. Clamp the sample such that a 1.0 cm long portion of the sample (portion to be compressed) extends vertically above the horizontal surface of the clamp.
3. Center T-rod on sample with the push rod perpendicular to the long side of the sample surface that is parallel to the horizontal surface of the clamp.
4. Lower T-rod until it exerts a 4.5±0.5 gram force on the sample.
5. Compress the surface of the product for 5.0 mm at a crosshead speed of 2 inches/minute (51 millimeters/minute).
6. Record the peak force.
7. Repeat for at least 10 samples.

Calculations and Reporting

Calculate and report the mean and standard deviation of the peak force for each sample evaluated.

Water Dispersibility

Apparatus

| | |
|---|---|
| Stirrer | Magnetic, Thermolyne type Model S7225 or 7200 (no substitutions). Permanently inscribe a circle 3.5 inches (8.9 centimeter) on the top surface of the stirrer. The center of the circle must be coincident with the geometric center of the stirrer. |
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL is suitable |
| Beaker | Kimax brand 2000 milliliter with spout (no substitution), Inscribe a fill mark at a height of 5.6 inches (14.3 centimeters) from the flat bottom of the beaker. Do not use any beaker not having a flat bottom. |

Test Setup
1. Fill the beaker to the fill mark with 73+3° F. tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure
1. Hold a sample 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch.
4. Record the time required until the simple separates into at least two pieces.
5. Repeat steps 1 through 4 with an additional 3 samples.

Calculation and Reporting

Calculate and report the mean and standard deviation of the water dispersibility time for the four samples tested.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An interlabial absorbent structure for wearing within an interlabial space, said interlabial space having opposed walls, said interlabial absorbent structure having a longitudinal centerline, a body contacting surface, and an opposed rear surface and comprising:

a pair of absorbent panels, each panel having a size so that said interlabial absorbent structure fits within said interlabial space when said absorbent structure is worn, a proximal edge, a distal edge, and a pair of opposed end edges, wherein each of said panels comprises a plurality of plies, said plurality of plies being joined at said distal edge of said panel and each of said panels has sufficient flexibility that it at least partially conforms to a surface of said wall and is capable of maintaining contact with said surface when said interlabial absorbent structure is worn;

an isthmus which joins said proximal edges of said panels, said distal edges being free to rotate about said isthmus, said isthmus being positioned furthest inward into said interlabial space when said interlabial absorbent structure is worn, wherein said isthmus comprises a densified portion of the materials comprising said panels; and an extraction means joined to said rear surface of said interlabial absorbent structure opposite the body surface of said isthmus.

2. An interlabial absorbent structure for wearing within an interlabial space, said interlabial space having opposed walls, said interlabial absorbent structure having a longitudinal centerline, a body contacting surface, and an opposed rear surface and comprising:

a pair of absorbent panels, each panel having a size so that said interlabial absorbent structure fits within said interlabial space when said absorbent structure is worn, a proximal edge, a distal edge, and a pair of opposed end edges, wherein each of said panels comprises a plurality of plies, said plurality of plies being joined at said distal edge of said panel and each of said panels has sufficient flexibility that it at least partially conforms to a surface of said wall and is capable of maintaining contact with said surface when said interlabial absorbent structure is worn;

an isthmus which joins said proximal edges of said panels, said distal edges being free to rotate about said isthmus, said isthmus being positioned furthest inward into said interlabial space when said interlabial absorbent structure is worn, wherein said isthmus comprises an extension of the materials which comprise said panels beyond said proximal edges, said panels being joined at said proximal edges by a plurality of discrete securment means; and an extraction means joined to said rear surface of said interlabial absorbent structure opposite the body surface of said isthmus.

3. An interlabial absorbent structure for wearing within an interlabial space, said interlabial space having opposed walls, said interlabial absorbent structure having a longitudinal centerline, a body contacting surface, and an opposed rear surface and comprising:

a pair of absorbent panels, each panel having a size so that said interlabial absorbent structure fits within said interlabial space when said absorbent structure is worn, a proximal edge, a distal edge, and a pair of opposed end edges, wherein each of said panels comprises a plurality of plies, said plurality of plies being joined at said distal edge of said panel and each of said panels has sufficient flexibility that it at least partially conforms to a surface of said wall and is capable of maintaining contact with said surface when said interlabial absorbent structure is worn;

an isthmus which joins said proximal edges of said panels, said distal edges being free to rotate about said isthmus, said isthmus being positioned furthest inward into said interlabial space when said interlabial absorbent structure is worn; and an extraction means joined to said rear surface of said interlabial absorbent structure opposite the body surface of said isthmus, wherein said extraction means comprises a tab.

* * * * *